United States Patent [19]

Cooper et al.

[11] Patent Number: 4,916,238

[45] Date of Patent: Apr. 10, 1990

[54] PROCESS FOR PREPARING ALLENIC PROSTANOIC ACID DERIVATIVES

[75] Inventors: Gary F. Cooper, Portola Valley; Colin C. Beard, Palo Alto; David Y. Jackson, Oakland; Douglas L. Wren, Palo Alto, all of Calif.

[73] Assignee: Syntex (U.S.A.) Inc., Palo Alto, Calif.

[21] Appl. No.: 283,644

[22] Filed: Dec. 13, 1988

[51] Int. Cl.[4] ............................................. C07F 7/18
[52] U.S. Cl. .................................... 549/214; 556/441
[58] Field of Search ........................ 549/214; 556/441

[56] References Cited

U.S. PATENT DOCUMENTS

| | | | |
|---|---|---|---|
| 3,879,438 | 4/1975 | Crabbe et al. | 560/121 |
| 3,985,791 | 10/1976 | Muchowski et al. | 560/55 |
| 4,418,206 | 11/1983 | Wren | 560/55 |
| 4,578,505 | 3/1986 | Collins et al. | 560/113 |
| 4,600,785 | 7/1986 | Cooper et al. | 549/214 |
| 4,689,419 | 8/1987 | Collins et al. | 549/214 |
| 4,778,904 | 10/1988 | Cooper | 549/214 |

OTHER PUBLICATIONS

Tetrahedron Letters No. 51, pp. 4615–4618, (1985).
J. Am. Chem. Soc., vol. 106, 3368–3370, (1984).

Primary Examiner—Richard L. Raymond
Assistant Examiner—Ba K. Trinh
Attorney, Agent, or Firm—Brian Lewis; Tom M. Moran; Alan M. Krubiner

[57] ABSTRACT

This invention relates to a novel process for making an allenic prostanoic acid derivative in the form of a single stereoisomer, or a mixture of stereosiomers, represented by the formula (I):

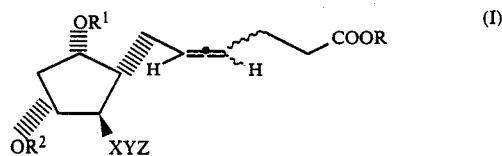

wherein R is lower alkyl, $R^1$ is a protecting group which can be selectively removed in the presence of $R^2$, $R^2$ is an acid-labile, base-stable protecting group, X is $-(CH_2)_2-$, trans $-CH=CH-$ or $-C\equiv C-$, Y is $-C(R^3)(OR^2)CH_2-$, in which $-OR^2$ is in the $\alpha$ or $\beta$ configuration and $R^3$ is hydrogen or methyl, Z is alkyl, or phenyl, benzyl or phenoxy each optionally substituted on the phenyl ring, and the wavy lines represent the $\alpha$ or $\beta$ configuration with the proviso that when one wavy line is $\alpha$ the other is $\beta$.

18 Claims, No Drawings

PROCESS FOR PREPARING ALLENIC PROSTANOIC ACID DERIVATIVES

BACKGROUND OF THE INVENTION

1. Field of the Invention

This invention relates to a novel process for the synthesis of certain allenic prostanoic acid derivatives, such derivatives being useful as intermediates in the preparation of synthetic prostaglandins which have the utility, for example, of gastric antisecretory activity.

2. Related Disclosures

Various methods for the preparation of allenes and allenic prostanoic acid derivatives are exemplified in the patent and chemical literature. See, for example, U.S Pat. Nos. 3,879,438; 3,985,791; 4,418,206; 4,578,505; *Tetrahedron Letters*, 1975, pp 4615-4618, *J.A.C.S.*, 1984, Vol. 106, 3368-3370. These references are variously concerned with the preparation of allenes via rearrangement of a propargylic ester with the requisite number of carbon atoms already in place by reaction with a lithium diorganocuprate. A method more closely related to the present invention is disclosed in U.S. Pat. No. 4,600,785, which describes the preparation of one embodiment of the intermediate of formula (2) in a racemic or optically pure form, and its subsequent two-carbon homologation accompanied by allene formation, by reaction with a trialkylorthoacetate (Claisen Rearrangement). However, to get to the desired corresponding embodiment of the compound of formula (I) it is then necessary to insert one more carbon atom between the allene moiety and the carboxyl group, a procedure involving four more steps.

The process described herein provides a more efficient method for the preparation of allenic prostanoic acid derivatives by three-carbon homologation of an intermediate of formula (2) with concomitant allene formation.

The disclosures of these, and all other documents referred to throughout the specification, are herein incorporated by reference.

SUMMARY OF THE INVENTION

In a first aspect, this invention relates to a process for producing an allenic prostanoic acid derivative in the form of a single stereoisomer, or a mixture of stereoisomers, represented by the formula (I):

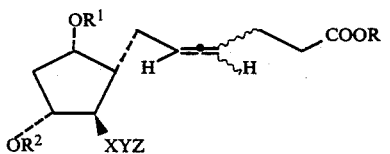

wherein R is lower alkyl of 1-6 carbon atoms, $R^1$ is a protecting group which can be selectively removed in the presence of $R^2$, $R^2$ is an acid-labile, base stable protecting group, X is —(C$_2$)$_2$—, trans —CH=CH— or —C≡C—, Y is —C(R$^3$)(OR$^2$)CH$_2$—, in which —OR$^2$ is in the $\alpha$ or $\beta$ configuration and $R^3$ is hydrogen or methyl, Z is alkyl of one to ten carbon atoms, or phenyl, benzyl or phenoxy each optionally substituted on the phenyl ring by one or two substituents chosen from lower alkyl of one to three carbon atoms, lower alkoxy of one to three carbon atoms, fluoro, chloro or trifluoromethyl; and the wavy lines represent the $\alpha$ or $\beta$ configuration with the proviso that when one way line is $\alpha$ the other is $\beta$, from propargyl alcohols of the formula (2). The process may be represented schematically:

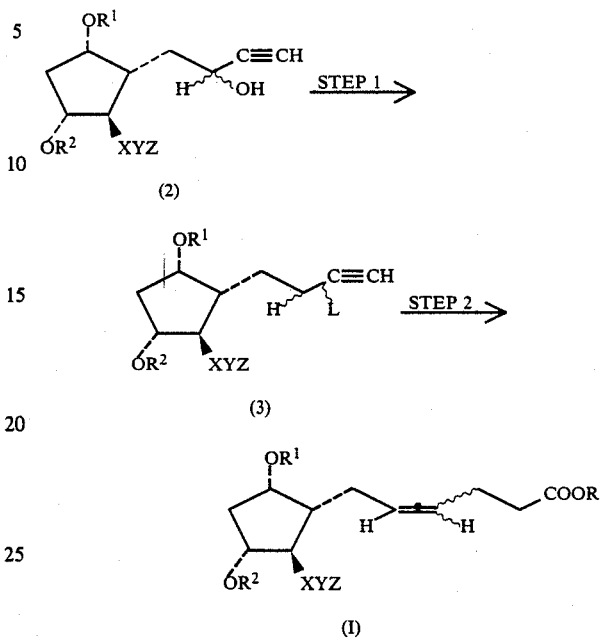

wherein R, $R^1$, $R^2$, X, Y and Z are as defined above and L is a leaving group. An important feature of this process is that in Step 2 reaction of a single stereoisomer or mixture of stereoisomers of the compound of formula (3) leads to the corresponding single stereoisomer or mixture of stereoisomers of formula (I) with predictable stereochemistry.

In a second aspect, the invention relates to novel compounds of the formula (3), which are useful as intermediates in the process herein.

DETAILED DESCRIPTION OF THE INVENTION

Definitions

As used herein:

Formulas having an allene group are represented herein as having substituents on one end of the allene group which are oriented at 90° to those on the other. When the allene group has three different substituents, as in formula (I), the allene moiety is rendered asymmetric.

The terms "$\alpha$ and $\beta$" indicate the specific stereochemical configuration of a substituent at an asymmetric carbon atom in a chemical structure as drawn. Thus "$\alpha$", denoted by a broken line, indicates that the group at the position in question is below the general plane of the molecule as drawn, and "$\beta$", denoted by a bold line, indicates that the group at the position in question is above the general plane of the molecule as drawn.

The double bond at the carbon numbered 13 in these formulas (where present) has the trans configuration, as in the natural PGE and PGF series prostaglandins.

The compounds of this invention possess asymmetric centers and thus can be produced as racemic or non-racemic mixtures or as individual enantiomers. The individual enantiomers may be obtained by resolving a racemic or non-racemic mixture of an intermediate at some appropriate stage of the synthesis. It is understood that the racemic or non-racemic mixtures and the individual enantiomers are encompassed within the scope of the present invention.

Formula (I), (illustrated below using the example where Y is —CH(OR$^2$)CH$_2$—), includes any single structure (Ia, Ib, Ic and Id), all permutations of two or three components in any proportions, and mixtures of all four components in any proportions.

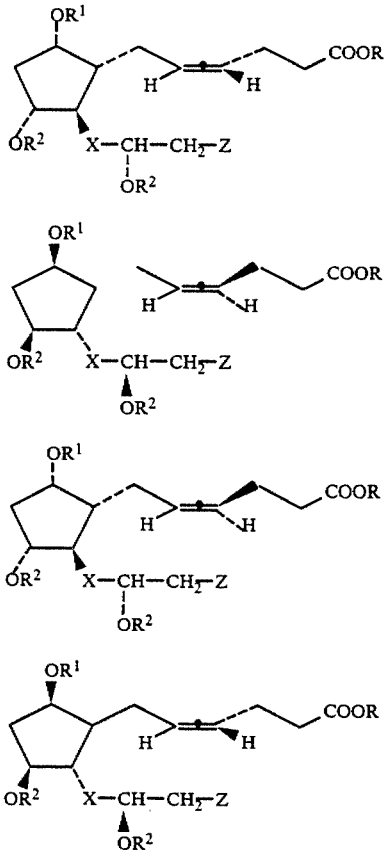

Any individual component may be prepared by processes described below starting from the appropriate individual enantiomers of the propargylic alcohol of formula (2) in Reaction Scheme I. Mixtures of Ia, Ib, Ic and Id in any proportion are produced starting from the appropriate racemic or non-racemic modification of the compound of formula (2).

For the sake of simplicity only one enantiomer, i.e., the enantiomer having the natural prostaglandin configuration, will be depicted in the description of the process. However, it is to be understood that the racemic and non-racemic mixtures and the individual unnatural enantiomers are also encompassed thereby, they being obtained by starting with the corresponding racemic or non-racemic mixture or unnatural enantiomer.

The natural configurations are represented by the formula Ia and Ic. The unnatural configurations are represented by the formula Ib and Id.

The term "mixture", as applied to formula (I) is defined in the present application as any combination of all four components (of formula Ia, Ib, Ic and Id as depicted above) in any proportions and all permutations of any two or three of the four components in any proportions.

The use of the symbol "R" or "S" preceding a substituent designates the absolute stereochemistry of that substituent according to the Cahn Ingold-Prelog rules [see Cahn et al., Angew. Chem. Inter. Edit., Vol. 5, p. 385 (1966), errata p. 511; Cahn et al., Angew. Chem., Vol. 78, p. 413 (1966); Cahn and Ingold, J. Chem. Soc., (London), 1951, p. 612; Cahn et al., Experientia, Vol. 12, p. 81 (1956); Cahn J. Chem. Educ., Vol. 41, p. 116 (1964)]. Because of the interrelation of the designated substituent with the other substituents in a compound having α or β prefixes, the designation of the absolute configuration of one substituent fixes the absolute configuration of all substituents in the compound and thus the absolute configuration of the compound as a whole.

R$^1$ is defined as "a protecting group which can be selectively removed in the presence of R$^2$". Such a group, useful for the protection of hydroxy, may be any ether-forming group which will not be hydrolyzed when treated with an acid, yet will be hydrolyzed back to the original hydroxy group under mild conditions which will not result in degradation of the desired product. This group is best exemplified by —SiR$_4$R$_5$R$_6$ where R$_4$, R$_5$ and R$_6$ are lower alkyl, phenyl or arylalkyl except that all three may not be simultaneously methyl. For the purpose of this invention, lower alkyl means a radical of 1 to 6 carbon atoms. Arylalkyl is a radical wherein alkyl has the same meaning as lower alkyl and aryl is exemplified by but not limited to phenyl, alkyl substituted phenyl, and naphthyl. Particularly preferred silyl groups are t-butyldimethylsilyl, triisopropylsilyl, triphenylsilyl, t-butyldiphenylsilyl and 2,4,6-tri-t-butylphenoxydimethylsilyl radicals. Such groups are preferably removed by treatment with fluoride ions, for example tetra n butylammonium fluoride or aqueous hydrofluoric acid.

R$^2$ is defined as an "acid-labile, base-stable protecting group". Such a group, useful for the protection of hydroxy, may be any ether-forming group which will not be hydrolyzed when treated with a strong aqueous base such as sodium or potassium hydroxide or fluoride ions. yet will be hydrolyzed back to the original hydroxy group by acid under mild conditions which will not result in degradation of the desired product. Examples of groups which are acid-labile yet base-stable are tetrahydrofuranyl, tetrahydropyranyl, 1-ethoxyethyl and the like. Excluded from this definition are alkyl ethers, benzyl ether and alkylaryl ethers, and the like. The conditions normally required to effect acid hydrolysis of these latter ethers would cause product degradation during the hydrolysis process, if in fact their hydrolysis would be effected by acid to all. It is preferred to protect the C-11 and C-15 hydroxyl groups with tetrahydropyranyl, tetrahydrofuranyl or 1-ethoxyethyl.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Epimers" are diastereoisomers which differ only in the configuration of one asymmetric center.

"Racemic mixture" means a mixture containing equal parts of individual enantiomers. "Non-racemic mixture" is a mixture containing unequal parts of individual enantiomers.

"Alkyl" means a branched or unbranched saturated hydrocarbon chain containing 1 to 10 carbon atoms, such as methyl, ethyl, propyl, tert-butyl, n-hexyl, 2-methylheptyl, n-decyl and the like;

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —OR wherein R is lower alkyl as herein defined.

"Halo" means fluoro, chloro, bromo or iodo, unless otherwise indicated.

"Cation-ligand complexant" refers to compounds such as hexamethylphosphoric triamide, N,N'-dimethyl-N,N'-ethylene urea or N,N'-dimethyl-N,N'-propylene urea, and the like, as discussed in *Helvetica Chimica Acta*, Vol. 65, 385–391 (1982).

A "leaving group" means a group capable of being displaced by a nucleophile in a chemical reaction. In particular this definition is intended to cover the reaction where an allene is formed by the displacement of a leaving group adjacent to an acetylene, for example a propargylic acetate. Other leaving groups are, for example, chloro, bromo, iodo, sulfonate ester, sulfinate ester, carbamate and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

The compounds of this invention are named as derivatives of the upper side chain. That is, the compounds of formula (2) and (3) are named as derivatives of but-1-yne. For example a compound of the formula:

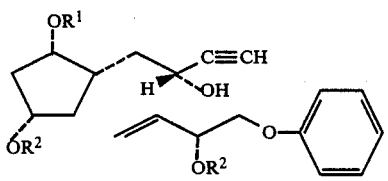

(2a)

where $R^1$ is t-butyldimethylsilyl and $R^2$ is tetrahydropyranyl is named (3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]-cyclopent-1α-yl]-but-1-yn-3α-ol.

Similarly, compounds of formula (I) are named as derivatives of hepta-4,5-dienoic acid. Thus the following example of a compound of formula (I):

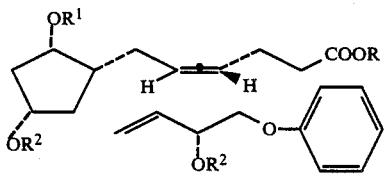

(I)

where is methyl, $R^1$ is t-butyldimethylsilyl and $R^2$ is tetrahydropyranyl is named:
methyl (4,5,6R)-7-[5α-t-butyl-dimethylsilyloxy-3α-(tetrahydro-pyran-2-yloxy)-2β-[3α-(tetrahydropyran-2-yloxy)-4-phenoxy-1(E) buten-1-yl]-cyclopent-1α-yl]-4,5-heptadienoate.

Starting Materials

The starting compound of formula (2) is prepared from the appropriate lactone of formula (4):

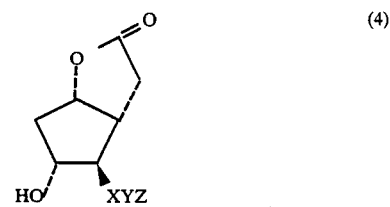

(4)

where X, Y and Z are as defined above.

The sequence of reactions necessary to convert the compound of formula (4) to the compound of formula (2) as a single stereoisomer or a racemic or non-racemic mixture (where X is trans —CH=CH—, Y is α —CH(OH)CH$_2$—, Z is phenoxy and $R^3$ is hydrogen) is disclosed in U.S. Pat. No. 4,600,785, and in allowed U.S. patent application No. 002,339, filed 1/9/87. Numerous references show the preparation of lactones of formula (4): see, for example, J. Am. Chem. Soc., 91, 5675 (1969), U.S. Pat. No. 4,303,907 to Nelson, U.S. Pat. No. 4,321,275 to Bowler et al. Thus it is clear that a person of ordinary skill could combine the above references with the teachings of U.S. Pat. No. 4,600,785 to prepare any compound of formula (2).

The Process

The novel process for preparing the compounds of formula (I), starting from the compounds of formula (2), is shown in Reaction Scheme I.

REACTION SCHEME I

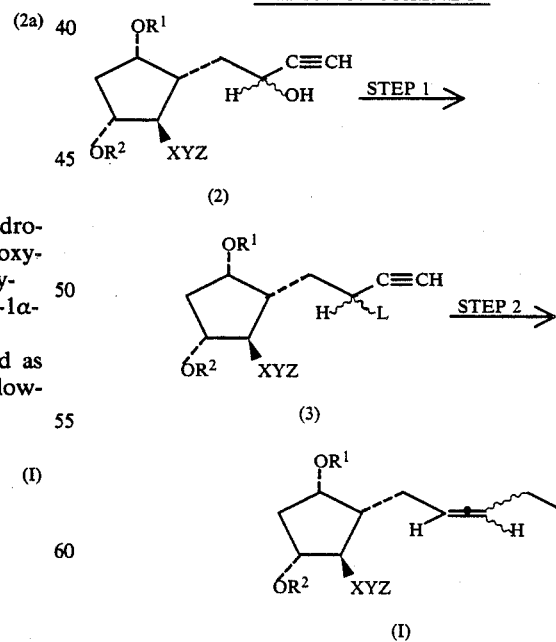

wherein R, $R^1$, $R^2$, X, Y, Z are as defined above, and L is a leaving group.

The reaction of Step 1, in its broadest aspect, comprises converting the 3-hydroxy group of a compound of formula (2) to the leaving group L of a compound of formula (3). For clarity, this step is illustrated in two separate Reaction Schemes, IA and IB shown below, to better demonstrate that such a conversion may proceed by two different paths, depending upon the reagents and reaction conditions employed.

Reaction Scheme IA shows the conversion of the hydroxy group to a leaving group L with retention of configuration. For the configuration to be retained, L is formed by replacing the hydrogen of the 3-hydroxy group to give an ester, preferably an acetate, or a sulfonate ester. sulfinate ester, a carbamate or the like. as shown below.

Reaction Scheme IB shows the conversion of the hydroxy group to a leaving group L with inversion of configuration. An example of inversion of configuration is found when L is formed by displacement of the 6-hydroxy group to give a 6-halo compound.

For convenience, the compound of formula (2) where the hydroxy is in the α orientation is represented as (2a), and where the hydroxy is in the β orientation as (2b). Similarly, the compound of formula (3) where L is in the α orientation is represented as (3a), and where L is in the β orientation as (3b).

Reaction Scheme IA shows Step 1 wherein the orientation at the 3-position is retained. Thus a compound of formula (2a) (i.e. with a 3α-hydroxy group) gives a compound of formula (3a) (i.e. with a 3α-leaving group).

REACTION SCHEME IA

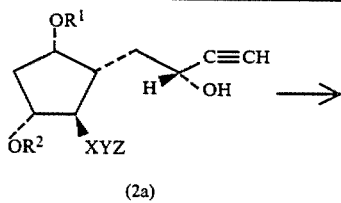

(2a)

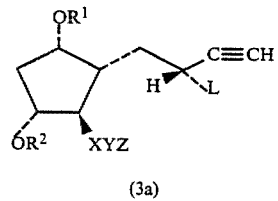

(3a)

In this reaction scheme L is an ester, preferably an acetate, or a sulfonate ester, sulfinate ester, a carbamate or the like. For example, reaction of a compound of formula (2) with acetic anhydride or an acetyl halide converts the 3-hydroxy group to a 3-acetate, reaction of (2) with N,N-dimethylcarbamyl chloride gives a 3-dimethylcarbamate, reaction of (2) with an alkylsulfinyl chloride gives a 3-sulfinate ester, or reaction of (2) with an alkyl or aryl sulfonyl halide, such as methanesulfonyl chloride or p-toluenesulfonyl chloride, leads to a preferred leaving group, the 3-sulfonate ester. For example, to prepare the compound of formula (3a) where L is an alkylsulfonate ester, the compound of formula (2a) is dissolved in an inert solvent, such as diethyl ether, tetrahydrofuran, ethyl acetate, toluene, acetonitrile, chloroform or preferably dichloromethane in admixture with about 1–10 molar equivalents, preferably about 2 molar equivalents, of an inorganic base such as sodium carbonate, potassium bicarbonate or the like, or preferably a tertiary organic base, such as pyridine, N-methylpiperidine and the like, most preferably triethylamine. The mixture is cooled to about −60° to 25° C., preferably about −30° C., and about 1–4 molar equivalents, preferably about 1.5 molar equivalents, of an alkylsulfonyl halide, preferably methanesulfonyl chloride, and the mixture stirred for about 10 minutes to 2 hours, preferably about 30 minutes, allowing the temperature to rise to about 0° C. Water is then added while allowing the temperature to rise to about 25° C. The compound of formula (3a) where L is an alkylsulfonate ester, preferably methanesulfonate ester, is then separated and purified by conventional means. Similarly the compounds of formula (3a) where L is an ester, sulfinate ester, carbamate and the like are prepared.

Alternatively, the compound of formula (2a) is dissolved in a tertiary organic base, preferably pyridine, at a temperature of about 0°–40° C., preferably about 25° C., and about 1–10 molar equivalents is added, preferably about 4 molar equivalents, of an arylsulfonyl halide, preferably p-toluenesulfonyl chloride, or an acyl anhydride, preferably acetic anhydride, and the mixture stirred for about 2–24 hours, preferably about 12 hours, at about 25° C. Water is added and the compound of formula (3a) is then separated and purified by conventional means.

Likewise, a compound of formula (2b) (i.e. with a 3β-hydroxy group) in Reaction Scheme IA gives a compound of formula (3b) (i.e. with a 3β-leaving group). Also, starting with diastereoisomeric, racemic or non-racemic mixtures of the compound of formula (2) gives a corresponding diastereoisomeric, racemic or non-racemic mixture of the compound of formula (3) with retention of configuration at the 3-position.

In contrast to the procedures described in Reaction Scheme IA, Reaction Scheme IB shows Step 1 wherein the configuration at the 3-carbon atom is inverted. Thus a compound formula (2a) (i.e. with a 3α-hydroxy group) gives a compound of formula (3b) (i.e. with a 3β-leaving group):

REACTION SCHEME IB

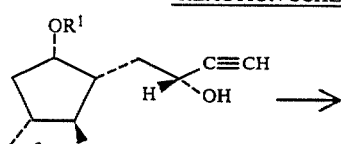

(2a)

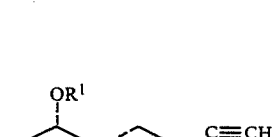

(3b)

In this Reaction Scheme L is chloro, bromo, iodo or tosylate.

In Reaction Scheme IB, the compound of formula (2a) is reacted with an agent capable of displacing the 3-hydroxy group to give a halo group or tosylate. One example of such a conversion to a halide is reaction of a compound of formula (2a) with triphenylphosphine and a carbon tetrahalide. Typically, the compound of formula (2a) is dissolved in an inert solvent as defined above, preferably diethyl ether/acetonitrile mixture, at a temperature of about 0°-40° C., preferably about 25° C., and about 1-4 molar equivalents, preferably about 2 molar equivalents, of the appropriate carbon tetrahalide, for example carbon tetrachloride, is added, followed by about 1-10 molar equivalents, preferably about 4 molar equivalents, of a tertiary organic base as defined above, preferably pyridine. To this solution is then added about 1-4 molar equivalents, preferably about 2 molar equivalents, of triphenylphosphine and the mixture is stirred for about 30 minutes to 4 hours, preferably about 1 hour. The compound of formula (3b) is then separated and purified by conventional means, for example chromatography. This is the preferred method for the preparation of the 3-chloro, 3-bromo and 3-iodo compounds of formula (3b).

An alternative procedure for the preparation of the compounds of formula (3b) is by employing "Mitsunobu" reaction conditions, i.e. reaction of the compound of formula (2a) with triphenylphosphine, diethyl azodicarboxylate and an alkylating agent or sulfonate salt. The "Mitsunobu Reaction" is described in more detail in, for example, *Synthesis*, 1981, 1-28. Typically, the compound of formula (2a) is dissolved in an inert solvent as defined above, preferably toluene, at a temperature of about 0°-40° C., preferably about 25° C., and about 1-4 molar equivalents, preferably about 2 molar equivalents, of triphenylphosphine is added, followed by about 1-4 molar equivalents, preferably about 2 molar equivalents, of an alkylating agent or sulfonate salt, for example methyl iodide or pyridinium tosylate. To this solution is then added about 1-4 molar equivalents, preferably about 2 molar equivalents, of diethyl azodicarboxylate and the mixture is stirred for about 10 minutes to 2 hours, preferably about 30 minutes. The compound of formula (3b) is then separated and purified by conventional means, for example chromatography. This is an alternative method for the preparation of the 3-iodo and 3-tosylate compounds of formula (3b).

Likewise, a compound of formula (2b) (i.e. with a 3β-hydroxy group) in Reaction Scheme IB gives a compound of formula (3a) (i.e. with a 3α-leaving group). Also, a diastereoisomeric, racemic or non-racemic mixtures of the compound of formula (2) gives a corresponding diastereoisomeric, racemic or non-racemic mixture of the compound of formula (3) with inversion of configuration.

Thus it can be seen that in Step 1, starting from a 3α-hydroxy compound of formula (2a), compounds of formula (3) with a 3α-leaving group or a 3β-leaving group may be prepared, depending upon the reagents and reaction conditions employed. Similarly, starting with a 3β-hydroxy compound of formula (2b), compounds of formula (3) with a 3α-leaving group or a 3β-leaving group may be prepared. Likewise, mixtures of 3α- and 3β-compounds of formula (2) give mixtures of 3α- and 3β-compounds of formula (3) with retention or inversion of configuration as desired.

In addition, 3α-hydroxy compounds of formula (2a) may be converted to 3β-hydroxy compounds of formula (2b), and vice-versa, by applying the above "Mitsunobu" reaction conditions, i.e. reacting with diethyl azodicarboxylate and triphenylphosphine and hydrolyzing the ester thus formed. Thus any 3α or 3β compound of formula (3a) or (3b) can be obtained starting from either the 3α or the 3β compound of formula (2a) or (2b).

The reaction of Step 2, in its broadest aspect, comprises reacting compounds of formula (3) with a 2-carbo(lower alkoxy)ethylzinc iodide in the presence of a copper (I) salt, as shown in Reaction Scheme IC. The Reaction Scheme shows both the reaction of a compound of formula (3a) (i.e. with a 3α-leaving group) and of a compound of formula (3b) (i.e. with a 3β-leaving group) to fully illustrate an important novel feature of this invention, namely the absolute predictability of the stereochemistry of the 4-allene moiety in the product of formula (I) arising from reaction of a compound of formula (3) of known stereochemistry, i.e. a compound of formula (3a) or (3b), with a 2-carbo(lower alkoxy)ethylzinc iodide.

REACTION SCHEME IC

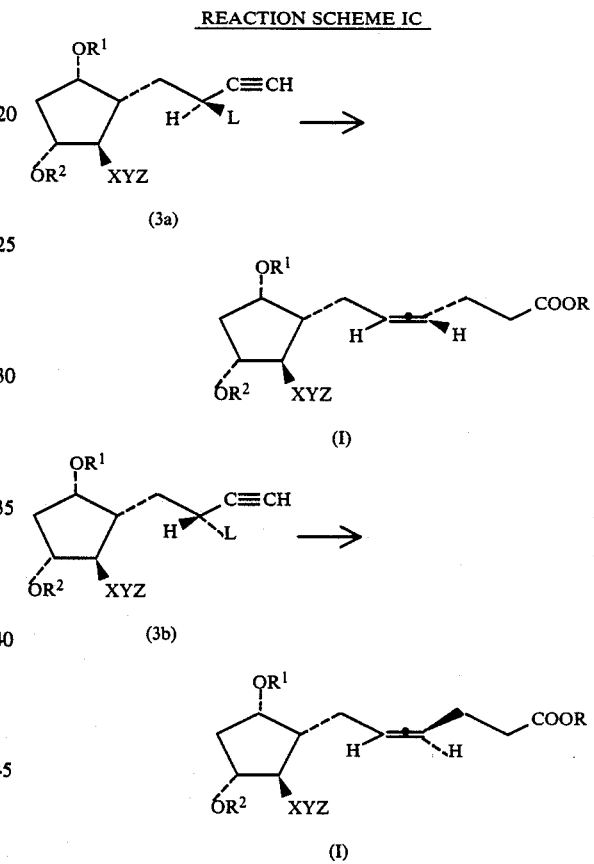

In the above Reaction Scheme, R, R¹, R², X, Y, Z and L are as defined above.

The conversion of the compound of formula (3) to the compound of formula (I) is accomplished by reaction of the compound of formula (3), in the presence Of a copper (I) salt, with a 2-carbo(lower alkoxy)ethylzinc iodide, preferably 2-carbomethoxyethylzinc iodide, which is generated in situ by reaction of the corresponding iodo ester (an alkyl 3-iodopropionate) with zinc-copper couple. Typically, about 2–6 molar equivalents, preferably about 3.5 molar equivalents, of zinc-copper couple is stirred with about 1–4 molar equivalents, preferably about 2.1 molar equivalents, of an alkyl 3-iodopropionate, preferably methyl 3-iodopropionate, in an inert solvent such as benzene, ethylbenzene, xylene and the like, preferably toluene, containing about 10% of an aprotic solvent such as dimethylacetamide. The reaction is conducted at a temperature of about 40°-90° C., preferably about 60° C., for about 30 minutes to 8 hours, preferably about 2 hours. The reaction mixture is then cooled to about 20°-55° C., preferably about 30° C., and about 0.05-5 molar equivalents, preferably about 2.1 molar equivalents, of a copper(1)salt added, preferably copper bromide-dimethyl sulfide complex or copper iodide, followed by about 1-5 molar equivalents, preferably about 2.1 molar equivalents, of a cation-ligand complexant such as hexamethylphosphoric triamide (HMPA), N,N'-dimethyl-N,N'-ethylene urea or N,N'-dimethyl-N,N'-propylene urea (DMPU). The cation-ligand complexant providing the highest yield is HMPA, but owing to the well known carcinogenic properties of HMPA the usual compound employed is DMPU. A toluene/dimethylacetamide solution containing about 1 molar equivalent of the compound of formula (3) is then added and the mixture maintained at a temperature of about 30°-55° C., preferably about 50° C., for about 30 minutes to 4 hours, preferably about 1 hour. When the reaction is substantially complete, the product is isolated and purified by conventional means, for example chromatography.

Thus a compound of formula (3a), i.e. with a 3α-leaving group, gives a compound of formula (I) with a 4β-allene group, and likewise a compound of formula (3b), i.e. with a 3β-leaving group, gives a compound of formula (I) with a 4α-allene group. Likewise, a compound of formula (3) which is a mixture of 3α- and 3β-compounds gives a corresponding mixture of 4β- and 4α-allenes of formula (I).

It can thus be seen that starting from an optically pure isomer of a compound of formula (3) one obtains an optically pure product of formula (I) of predictable stereochemistry, and diastereoisomeric, racemic or non-racemic mixture of isomers of a compound of formula (3) leads to a corresponding diastereoisomeric, racemic or non-racemic mixture of isomers of a compound of formula (I).

Utility

The compounds of formula (I) may be converted to allenic prostanoic acid derivatives useful, for example, for their gastric antisecretory activity, by methods well known in the chemical art. For example, U.S. Pat. No. 4,600,785 discloses a method for the preparation of PGE and PGF type of prostaglandins from compounds of formula (I) in which R is hydrogen or lower alkyl, $R^1$ is t-butyldimethylsilyl and $R^2$ is tetrahydropyran-2-yl, X is trans —CH=CH—, Y is —CH($OR^2$)$CH_2$—, in which —$OR^2$ is in the α or β configuration and $R^2$ is tetrahydropyran-2-yl and Z is phenoxy. Any compound of formula (I) may be converted in a similar manner to the corresponding PGE or PGF analog.

The following Examples illustrate the invention but are not intended to limit its scope.

EXAMPLE 1

Preparation of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-bromobut-1-yne and related compounds of formula (3)

A. To a solution of 1.0 g of (3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-ol (a compound of formula (2a)), 0.51 g of pyridine and 0.85 g of triphenylphosphine in 10 ml of acetonitrile was added a solution of 1.08 g of carbon tetrabromide in 10 ml of acetonitrile and the mixture stirred for 1 hour at 25° C. About 200 ml of diethylether was then added, the precipitate filtered off and the filtrate washed with water followed by brine. The organic layer was then dried over magnesium sulfate and the solvent removed under reduced pressure. The residue was chromatographed on 20 g of silica gel, eluting sequentially with 5% ethyl acetate/hexane to 10% ethyl acetate/hexane to yield 0.98 g of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3α-bromobut-1-yne.

B. Similarly, optionally replacing (3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-ol with other compounds of formula (2a) or (2b) and optionally replacing carbon tetrabromide with carbon tetrachloride or carbon tetraiodide, and following the procedure of paragraph A above, the following exemplary compounds of formula (3) are prepared:

(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-chlorobut-1-yne;

(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-iodobut-1-yne;

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl-3α-bromobut-1-yne;

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3-chlorobut-1-yne;

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3α-iodobut-1-yne;

(3S)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-3β-bromobut-1-yne;

(3S)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-3β-bromobut-1-yne;

(3S) 4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-3β-bromobut-1-yne;

(3S) 4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-3α-bromobut-1-yne;

(3R)-4-[5α-t-butyldimethylsilyloxy-3α-(tetrahydropyran-2-yloxy)-2β-[3α-(tetrahydropyran-2-yloxy)-4-phenoxy-but-1-yl]cyclopent-1α-yl]-3α-bromobut-1-yne;

(3R)-4-[5α-t-butyldimethylsilyloxy-3α(tetrahydropyran-2-yloxy)-2β-[3α-(tetrahydropyran-2-yloxy)-4-phenoxybut-1-yn-1-yl]cyclopent-1α-yl]-3α-bromobut-1-yne;

(3R)-4-[5α-t-butyldimethylsilyloxy-3α-(tetrahydropyran-2-yloxy)-2β-[3α-(tetrahydropyran-2-yloxy)-3β- methyl-4-phenoxy-1(E)-buten-1-yl]cyclopent-1α-yl]-3α-bromobut-1-yne; and (3R)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-3α-btomobut-1-yne.

EXAMPLE 2

Preparation of (3S)-4-[5-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-methanesulfonate and related compounds of formula (3)

A. A solution of 5.0 g of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent 1α-yl]-but-1-yn-3β-ol (a compound of formula (2b)) in 100 ml of dichloromethane was cooled to −30° C. under nitrogen and 1.64 g of triethylamine added with stirring, followed by 1.40 g of methanesulfonyl chloride in 10 ml of dichloromethane over a period of about 15 minutes, maintaining the temperature below −25° C. The reaction mixture was stirred at −30° C. for an additional 30 minutes, then allowed to warm to 0° C. Water (50 ml) was added and the mixture stirred for 15 minutes at 25° C. The organic layer was separated, washed with brine, dried over magnesium sulfate and the solvent removed under reduced pressure. The crude product of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-methanesulfonate was used in the next step with no further purification.

B. Similarly, replacing (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-ol with other compounds of formula (2a) or (2b) and following the procedure of paragraph A above, the following exemplary compounds of formula (3) are prepared:

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-methanesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-but-1-yn-3β-methanesulfonate;

(3R)-4-[5α-t-butyldimethylsilyloxy-3α-(tetrahydropyran-2-yloxy)-2β-[3α-(tetrahydropyran-2-yloxy)-4-phenoxybut-1-yn-1-yn]cyclopent-1α-yl]but-1-yn-3α-methanesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-but-1-yn-3β-methanesulfonate;

(3R)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-but-1-yn-3α-methanesulfonate;

(3S)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-but-1-yn-3β-methanesulfonate;

(3R)-4-[5α-t-butyldimethylsilyloxy-3α-(tetrayhydropyran-2-yloxy)-2β-[3α-(tetrahydropyran-2-yloxy)-3β-methyl-4-phenoxy-1(E)-buten-1-yl]cyclopent-1α-yl]-but-1-yn-3α-methanesulfonate;

(3S)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3β-methanesulfonate; and (3R)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3α-methanesulfonate.

EXAMPLE 3

Preparation of (3S)-4-[5α-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-p-toluenesulfonate and related compounds of formula (3)

A. A solution of 100 mg of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-ol (a compound of formula (2b)) in 2 ml of pyridine was cooled to 0° C. and 125 mg of p-toluenesulfonyl chloride added. The mixture was stirred at 25° C. overnight, then 10 ml of water added and the mixture stirred for 15 minutes. The product was extracted with dichloromethane, the solution dried over magnesium sulfate and solvent removed under reduced pressure. The residue was purified by preparative thin layer chromatography to yield 110 mg of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-p-toluenesulfonate.

B. Similarly, replacing (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-ol with other compounds of formula (2a) or (2b) and following the procedure of paragraph A above, the following exemplary compounds of formula (3) are prepared:

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-but-1-yn-3β-p toluenesulfonate;

(3R)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3β-p-toluenesulfonate; and (3R)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3α-p-toluenesulfonate.

EXAMPLE 4

Preparation of
(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-iodobut-1-yne and related compounds of formula (3)

A. A solution of 1.0 g of (3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-ol (a compound of formula (2a)), 0.82 g of triphenylphosphine and 0.45 g of methyl iodide in 20 ml of toluene under nitrogen was stirred at 25° C. and 0.55 g of diethyl azodicarboxylate added in one portion. The mixture was stirred for 30 minutes then 5 ml of water added and the liquid phases transferred to a separating funnel. The remaining gum was dissolved in a minimum quantity of acetone, 200 ml of hexane added and the precipitate filtered off. The filtrate was combined with the mixture in the separating funnel, the organic layer separated and solvent removed under reduced pressure. The residue was chromatographed on silica gel, eluting with 3% ethyl acetate/hexane, to yield 1.1 g of (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-iodobut-1-yne.

B. Similarly, optionally replacing (3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-ol with other compounds of formula (2a) or (2b) and optionally replacing methyl iodide with an appropriate alkylating agent and following the procedure of paragraph A above, the following exemplary compounds of formula (3) are prepared:

(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-chlorobut-1-yne;

(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3β-iodobut-1-yne;

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3α-bromobut-1-yne;

(3R) 4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-3α-chlorobut-1-yne;

(3R)-4-[5α-t-butyldimethylsilyloxy-3α-(tetrahydropyran-2-yloxy)-2β-[3α-(tetrahydropyran-2-yloxy)-4-pheoxy-1(E)-buten-1-yl]cyclopent-1α-yl]-3α-iodobut-1-yne;

(3S)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-3α-btomobut-1-yne;

(3S)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-3β-bromobut-1-yne;

(3S)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-3β-bromobut-1-yne;

(3S)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-3β-bromobut-1-yne;

(3R)-4-[5α-t-butyldimethylsilyloxy-3α-(tetrahydropyran-2-yloxy)-2β-[3α-(tetrahydropyran-2-yloxy)-4-phenoxy but-1-yl]cyclopent-1α-yl]-3α-bromobut-1-yne;

(3R)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-3α-bromobut-1-yne;

(3R)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-3α-btomobut-1-yne;

(3R)-4-[5α-t-butyldimethylsilyloxy-3α-(tetrahydropyran-2-yloxy)-2β-[3α-(tetrahydropyran-2-loxy)-(1E)-octen-1-yl]cyclopent-1α-yl]-3α-bromobut-1-yne;

(3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-4-phenoxybut 1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-but-1-yn-3β-p-toluenesulfonate;

(3R)-4-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-but-1-yn-3α-p-toluenesulfonate;

(3S)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3β-p-toluenesulfonate; and (3R)-4-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-but-1-yn-3α-p-toluenesulfonate.

EXAMPLE 5

Preparation of methyl
(4,5,6R)-7-[5α-t-butyldimethylsilyloxy-3α-(tetrahydropyran-2-yloxy)-2β-[3α-(tetrahydropyran-2-yloxy)-4-phenoxy-1(E)-buten-1-yl]-cyclopent-1α-yl]-4,5-heptadienoate and related compounds of formula (I)

A. A mixture of 3.5 g of methyl 3-iodopropionate, 1.7 g of zinc-copper couple and 6 ml of dimethylacetamide in 75 ml of toluene was stirred at 60° C. for 2 hours. The reaction mixture was then cooled to 30° C. and 3.3 g of copper bromide/dimethyl sulfide complex added, followed by 2.1 g of N,N'-dimethyl N,N'-propylene urea. The mixture was stirred at 30° C. for 30 minutes, then 5.6 g of (3S)-4-[5α-t-butyldimethylsilyloxy-3α-(tetrahydropyran-2-yloxy)-2β-[3α-(tetrahydropyran-2-yloxy)-4-phenoxy-1(E) buten-1-yl]cyclopent-1α-yl]-but-1-yn-3β-methanesulfonate (a compound of formula (3b)) in 10 ml of toluene added. The reaction mixture was warmed to 50° C. and stirred until TLC shows that the reaction is complete, about 1 hour. The mixture was cooled to room temperature, 50 ml of water added, stirred for 15 minutes and filtered. The filtrate was washed with 50 ml of brine, dried over magnesium sulfate and the solvent removed under reduced pressure. The residue was chromatographed on 150 g of silica gel, eluting with 5% ethyl acetate/hexane followed by 10% ethyl acetate/hexane to give 4.45 g of methyl (4,5,6R)-7-[5α-t-butyldimethylsilyloxy-3α-(tetrahydro-pyran-2-yloxy)-2β-[3α-(tetrahydropyran-2-yloxy)-4-phenoxy-1(E)-buten-1-yl]-[cyclopent-1α-yl]-4,5-heptadienoate.

B. Similarly, replacing (3S)-4-[5α-t-butyldimethylsilyloxy-3α-(tetrahydropyran-2-yloxy)-2β-[3α-(tetrahydropyran-2-yloxy)-4-phenoxy-1(E)-buten-1-yl]-cyclopent-1α-yl]-but-1-yn-3β-methanesulfonate with other compounds of formula (3a) or (3b) and following the procedure of paragraph A above, the following exemplary compounds of formula (I) are prepared:

(4,5,6S)-7-[5α-t-butyldimethylsilyloxy-3α-(tetrahydropyran-2-yloxy)-2β-[3α-(tetrahydropyran-2-yloxy)-4-phenoxy-1(E)-buten-1-yl]cyclopent-1α-yl]-4,5-heptadienoate;

(4,5,6R)-7-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-4,5-heptadienoate;

(4,5,6S)-7-[5α-t-butyldimethylsilyloxy-3α-(tetrahydropyran-2-yloxy)-2β-[3α-(tetrahydropyran-2-yloxy)-3β-methyl-4-phenoxy-1(E)-buten-1-yl]cyclopent-1α-yl]-4,5-heptadienoate;

(4,5,6R)-7-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-4,5-heptadienoate;

(4,5,6S)-7-[5α-t-butyldimethylsilyloxy-3α-(tetrahydropyran-2-yloxy)-2β-[3α-(tetrahydropyran-2-yloxy)-(1E)-octen-1-yl]cyclopent-1α-yl]-4,5-heptadienoate;

(4,5,6R)-7-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-4,5-heptadienoate;

(4,5,6S)-7-[5α-t-butyldimethylsilyloxy-3α-(tetrahydropyran-2-yloxy)-2β-[3α-(tetrahydropyran-2-yloxy)-4-phenoxybut-1-yl]cyclopent-1α-yl]-4,5-heptadienoate;

(4,5,6R)-7-[5α-t-butyldimethylsilyloxy-3α-(tetrahydropyran-2-yloxy)-2β-[3α-(tetrahydropyran-2-yloxy)-4-phenoxybut-1-yn-1-yl]cyclopent-1α-yl]-4,5-heptadienoate; and (4,5,6S)-7-[5α-t-butyldimethylsilyloxy-3-(tetrahydropyran-2-yloxy)-2β-[3α-(tetrahydropyran-2-yloxy)-4-phenoxybut-1-yn-1-yl]cyclopent-1α-yl]-4,5-heptadienoate.

What we claim is:

1. A process for the preparation of an allenic prostanoic acid derivative in the form of a single stereoisomer, or a mixture of stereoisomers, represented by the following formula (I):

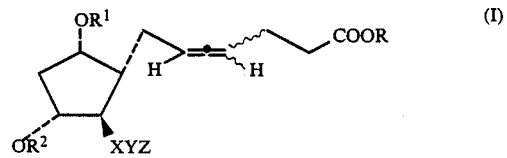

wherein
R is lower alkyl of 1-6 carbon atoms;
$R^1$ is a protecting group which can be selectively removed in the presence of $R^2$, wherein
$R^2$ is an acid-labile, base stable protecting group;
X is —(CH$_2$)$_2$—, trans —CH=CH— or —C≡C—;
Y is —C(R$^3$)(OR$^2$)CH$_2$— in which —OR$^2$ is in the α or β configuration and R$^3$ is hydrogen or methyl;
Z is alkyl of one to ten carbon atoms, or phenyl, benzyl or phenoxy, each optionally substituted on the phenyl ring of the phenyl, benzyl or phenoxy group by one or two substituents chosen from lower alkyl of one to three carbon atoms, lower alkoxy of one to three carbon atoms, fluoro, chloro or trifluoromethyl;
and the wavy lines represent the α or β configuration with the proviso that when one wavy line is α the other is β,
which comprises contacting a compound represented by the following formula (3):

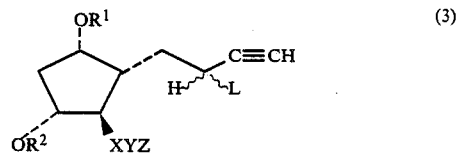

wherein R, $R^1$, $R^2$, X, Y, Z and the wavy lines are as defined above and L is a leaving group, with a 2-carbo(-lower-alkoxy)ethylzinc iodide in the presence of a copper(1) salt and a cation-ligand complexant.

2. The process of claim 1, wherein the compound of formula (3) is a single stereoisomer represented by the formula:

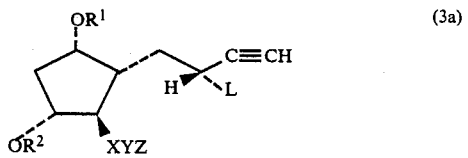

and the compound of formula (I) is a single stereoisomer represented by the formula:

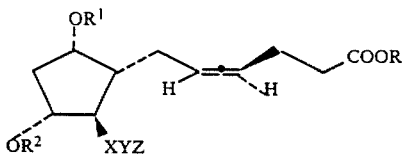 (I)

in which R, R$^1$, R$^2$, X, Y, Z and L are as defined above.

3. The process of claim 1, wherein the compound of formula (3) is a single stereoisomer represented by the formula:

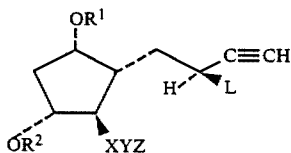 (3b)

and the compound of formula (I) is a single stereoisomer represented by the formula:

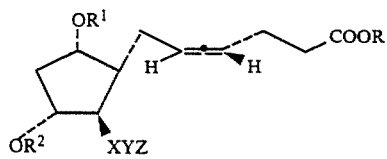 (I)

in which R, R$^1$, R$^2$, X, Y, Z and L are as defined above.

4. The process of claim 1, wherein the cation-ligand complexant is hexamethylphosphoric triamide, N,N'-dimethyl-N,N'-ethylene urea or N,N'-dimethyl-N,N'-propylene urea.

5. The process of claim 4, wherein the leaving group L is methanesulfonate, iodo or bromo.

6. The process of claim 5, wherein the 2-carbo(lower-alkoxy)ethylzinc iodide is 2-carbomethoxyethylzinc iodide.

7. The process of claim 6, wherein the copper(1)salt is cuprous bromide complexed with dimethyl sulfide.

8. The process of claim 7, wherein R$^1$ is t-butyldimethylsilyl, R$^2$ is tetrahydropyranyl, X is trans —CH=CH—, Y is —CH(OR$^2$)CH$_2$— where R$^2$ is tetrahydropyranyl, Z is phenoxy and L is bromo.

9. A process for the preparation of an allenic prostanoic acid derivative in the form of a single stereoisomer, or a mixture of stereoisomers, represented by the formula (I):

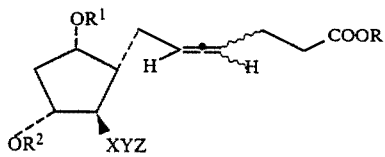 (I)

wherein
R is lower alkyl of 1–6 carbon atoms;
R$^1$ is a protecting group which can be selectively removed in the presence of R$^2$, wherein
R$^2$ is an acid-labile, base stable protecting group;
X is —(CH$_2$)$_2$—, trans —CH=CH— or —C≡C—;
Y is —C(R$^3$)(OR$^2$)CH$_2$— in which —OR$^2$ is in the α or β configuration and R$^3$ is hydrogen or methyl;

Z is alkyl of one to ten carbon atoms, or phenyl, benzyl or phenoxy, each optionally substituted on the phenyl ring of the phenyl, benzyl or phenoxy group by one or two substituents chosen from lower alkyl of one to three carbon atoms, lower alkoxy of one to three carbon atoms, fluoro, chloro or trifluoromethyl;
and the wavy lines represent the α or β configuration with the proviso that when one wavy line is α the other is β, which comprises:
(a) contacting a compound represented by the formula:

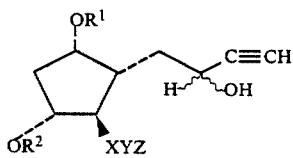 (2)

wherein R$^1$, R$^2$, X, Y and Z are as defined above, with a reagent capable of converting a hydroxy group to a leaving group, to give a compound represented by the formula:

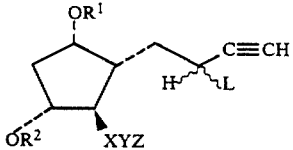 (3)

wherein R, R$^1$, R$^2$, X, Y, Z and the wavy lines are as defined above and L is a leaving group, followed by:
(b) contacting a compound represented by the formula (3) wherein R, R$^1$, R$^2$, X, Y, Z and the wavy lines are as defined above and L is a leaving group, with a 2-carbo(lower-alkoxy)ethylzinc iodide in the presence of a copper(1)salt and a cation-ligand complexant.

10. The process of claim 9, wherein the reagent converts the hydroxy group to a leaving group with retention of configuration.

11. The process of claim 10, wherein the reagent is a mixture of methanesulfonyl chloride and triethylamine.

12. The process of claim 9, wherein the reagent converts the hydroxy group to a leaving group with inversion of configuration.

13. The process of claim 12, wherein the reagent is a mixture of carbon tetrabromide and triphenylphosphine.

14. The process of claim 12, wherein the reagent is a mixture of diethyl azodicarboxylate, methyl iodide and triphenylphosphine.

15. The process of claim 9, wherein the compound of formula (3) is a single stereoisomer represented by the formula:

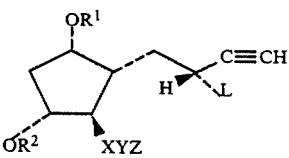 (3a)

and the compound of formula (I) is a single stereoisomer represented by the formula:

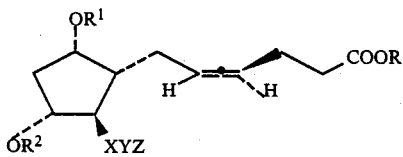
(I)

in which R, R¹, R², X, Y, Z and L are as defined above.

16. The process of claim 9, wherein the compound of formula (3) is a single stereoisomer represented by the formula:

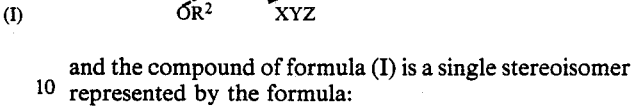
(3b)

and the compound of formula (I) is a single stereoisomer represented by the formula:

(I)

in which R, R¹, R², X, Y, Z and L are as defined above.

17. The process of claim 9, wherein the cation-ligand complexant is hexamethylphosphoric triamide, N,N'-dimethyl-N,N'-ethylene urea or N,N'-dimethyl-N,N'-propylene urea.

18. The process of claim 9, wherein the 2-carbo(lower-alkoxy)ethylzinc iodide is 2-carbomethyoxyethylzinc iodide.

* * * * *